United States Patent [19]
Petito

[11] Patent Number: 6,136,341
[45] Date of Patent: Oct. 24, 2000

[54] COLLAGEN CONTAINING TISSUE ADHESIVE

[76] Inventor: George D. Petito, The Hymed Group, 1890 Bucknell Dr., Bethlehem, Pa. 18015

[21] Appl. No.: 09/417,911

[22] Filed: Oct. 13, 1999

Related U.S. Application Data

[63] Continuation-in-part of application No. 09/032,031, Feb. 27, 1998, abandoned.

[51] Int. Cl.[7] .................................................. A61L 15/03
[52] U.S. Cl. .......................... 424/446; 424/443; 424/444; 424/445; 424/447; 424/448; 424/449
[58] Field of Search ............................ 424/443–4, 445–9

[56] References Cited

U.S. PATENT DOCUMENTS

| | | | |
|---|---|---|---|
| 4,216,204 | 8/1980 | Robertson | 424/95 |
| 4,455,302 | 6/1984 | Robertson | 424/177 |
| 4,759,354 | 7/1988 | Quarfoot | 524/21 |
| 4,804,745 | 2/1989 | Koepff et al. | 530/356 |
| 4,813,942 | 3/1989 | Alvarez | 424/446 |
| 4,837,024 | 6/1989 | Michaeli | 514/5 |
| 4,892,736 | 1/1990 | Goodson | 424/435 |
| 4,921,691 | 5/1990 | Stockel | 424/45 |
| 4,950,699 | 8/1990 | Holman | 424/445 |
| 5,081,106 | 1/1992 | Bentley et al. | 424/45 |
| 5,114,718 | 5/1992 | Damani et al. | 424/422 |
| 5,116,620 | 5/1992 | Chvapil et al. | 424/443 |
| 5,196,185 | 3/1993 | Silver et al. | 604/290 |
| 5,300,306 | 4/1994 | Alvarado et al. | 424/550 |
| 5,447,725 | 9/1995 | Damani et al. | 424/435 |
| 5,676,967 | 10/1997 | Williams et al. | 128/156 |

FOREIGN PATENT DOCUMENTS

| | | |
|---|---|---|
| 0 450 671 A1 | 10/1991 | European Pat. Off. . |
| 0 530 982 A1 | 3/1993 | European Pat. Off. . |

*Primary Examiner*—Jose' G. Dees
*Assistant Examiner*—Kathryne E. Shelborne
*Attorney, Agent, or Firm*—Richard C. Litman

[57] ABSTRACT

A tissue adhesive compound which may be a powder, gel, paste or film. The main ingredient is hydrolyzed Type I collagen having a molecular weight between 1,000 and 10,000. The collagen is preferably derived from a bovine source, especially calves under one year of age. The gel form preferably includes 60% hydrolyzed Type I collagen, and has anti-microbial properties not found in the powder form. In any form, the compound is administered to the cleaned wound site where it absorbs exudate, provides physical barrier to bacterial infestation, reduces pain and expedites wound healing. Removal of any compound remaining is unnecessary in subsequent dressing changes.

20 Claims, No Drawings

COLLAGEN CONTAINING TISSUE ADHESIVE

CROSS REFERENCE TO RELATED APPLICATION

This is a continuation-in-part of application Ser. No. 09/032,031 filed Feb. 27, 1998, and now abandoned or Oct. 14, 1999.

BACKGROUND OF THE INVENTION

1. Field of the Invention

The present invention relates to a method and composition for absorbing wound exudate and filling a wound.

2. Description of the Related Art

In order to protect a wound during the healing process, typically, a sterile dressing is used. The dressing is often treated with a tissue adhesive for speeding the healing process. An ideal tissue adhesive is biodegradable, nontoxic, and readily absorbed so that it does not hinder the healing process. Hydrolyzed collagen has been found to meet all these requirements.

As the principal structural protein, collagen is the main component of connective tissue. Type I collagen makes up more than 90% of these tissues, including periodontal ligaments and gingiva tissue. Amino acid composition and sequence determine the properties of collagen that make it suitable for wound healing, especially in acute or chronic wounds, and in dental applications. Favorable characteristics of collagen include high tensile strength, orientation of fibers, semipermeability of membranes, low antigenicity, positive effect on wound healing, and hemostatic properties.

Hydrolyzed collagen is defined as a collagen hydrolysate polypeptide having a molecular weight of 1,000 to 10,000 derived by hydrolysis. Hydrolyzed collagen is commercially available in powdered form, or as an aqueous solution. Commercial preparation is accomplished by one of three methods: alkaline hydrolysis, enzymatic hydrolysis, or acid hydrolysis. Any of these methods may be used to derive collagen from either a bovine or porcine source As suggested above, amino acid composition and sequence determine the beneficial healing qualities of collagen. Hydroxylysine and hydroxyproline are two amino acids found only in collagen and not other medical protein hydrolysates. Hydroxylysine is typically found in concentrations from 0.7 to 1.2% in hydrolyzed collagen, while hydroxyproline is found at concentrations of 12.1 to 14.5% Because hydrolyzed collagen is well suited for use as a tissue adhesive, and accelerates the healing process, there is a need for a wound dressing using hydrolyzed collagen.

The use of medical hydrolysates and collagen in wound healing has been the subject of previous patents. U.S. Pat. Nos. 4,216,204 and 4,455,302, which issued to Robertson on Aug. 5 1980 and Jun. 19, 1984 respectively, disclose a medical protein hydrolysate and processes for making and using the protein hydrolysate. The protein hydrolysate is made in powder or gel form from young poultry feet for application to traumatized areas.

Other patents disclose the use of collagen in various wound dressings. U.S. Pat. No. 4,759,354, which issued to Quarfoot on Jul. 26, 1988, discloses a wound dressing including a vapor-permeable layer and an absorbent adhesive layer containing collagen. U.S. Pat. No. 4,837,024, which issued to Michaeli on Jun. 6, 1989, discloses compositions, articles and methods for improving wound healing. The wound is contacted by a combined suspension of collagen and a chemotactic glycosaminoglycan for improved healing. U.S. Pat. No. 4,950,699, which issued to Holman on Aug. 21, 1990, discloses a wound dressing incorporating collagen in an adhesive layer. U.S. Pat. No. 5,081,106, which issued to Bentley, et al. on Jan. 14, 1992, discloses a wound dressing protocol utilizing collagen gelatin formed with iodine. U.S. Pat. No. 5,116,620, which issued to Chvapil, et al. on May 26, 1992, discloses an antimicrobial wound dressing, having a layer of collagen impregnated with lyophilized, stabilized chlorine-containing compounds. U.S. Pat. No. 5,196,185, which issued to Silver, et al. on Mar. 23, 1993, discloses a collagen-based wound dressing and method of application. The dressing uses type I and/or type III collagen in an aerosol delivery system.

Other compositions and methods for aiding wound healing have also been the subjects of previous patents, but are less related to the present invention. Examples of previous patents describing wound healing are diverse: U.S. Pat. No. 4,813,942 (three step wound treatment method and dressing therefor) which issued to Alvarez on Mar. 21, 1989; U.S. Pat. No. 4,921,691 (spray on wound dressing compositions) which issued to Stockel on May 1 1990; U.S. Pat. No. 5,300,306 (tissue-equivalent membrane from bovine esophageal tissue) which issued to Alvarado, et al. on Apr. 5, 1994; European patent document 0 530 982 A1 (wound dressing for deep wounds) published Mar. 10, 1993; and European patent document 0 450 671 A1 (wound dressing and method of preparing the same) dated Oct. 9, 1991.

Although many wound dressings exist, there is still a need for a wound dressing and method of application using the beneficial properties of hydrolyzed collagen. None of the above inventions and patents, taken either singularly or in combination, is seen to describe the instant invention as claimed.

SUMMARY OF THE INVENTION

The present invention is a method and composition used to promote healing. The compound may be a powder, gel, paste or film. The main ingredient is hydrolyzed Type I collagen. The collagen is preferably derived from a bovine source, especially calves less than one year of age. The gel form preferably includes 60% hydrolyzed Type I collagen, and has antimicrobial properties not found in the powder form. The powder form has better hemostatic qualities. In any form, the compound is administered to the cleaned wound site where it absorbs the exudate, provides a physical barrier to bacterial infestation, reduces pain and expedites wound healing.

Accordingly, it is a principal object of the invention to provide a favorable environment that encourages wound healing.

It is another object of the invention to protect the wound bed and newly formed tissue.

It is a further object of the invention to conform to any wound site.

It is an object of the invention to provide improved elements and arrangements thereof for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENTS

The present invention is a method and composition for filling a wound and absorbing exudate. The composition is a tissue adhesive medical hydrolysate that promotes wound healing. The composition may be in powder, paste or gel form, and may even be a film.

The method of applying the composition includes debriding and cleansing the wound site with saline according to traditional medical practice. Once the wound site is cleaned, the surrounding skin is dried while the wound site itself is left moist. A generous amount of the composition, despite form, is then applied to the wound site and surrounding area. A non-stick dressing, such as Telfa or gauze, is then applied. The dressing may be changed as needed, but at least once per day. If any amount of the composition remains in the wound site, it need not be removed before repeating the process. In some cases, the non-stick dressing may be eliminated because the composition will form a protective film if allowed to air dry.

The tissue adhesive properties of hydrolyzed collagen allow for faster healing and may, sometimes, negate the need for sutures or other closure means. In fact, the inventor has found the adhesive qualities of hydrolyzed collagen are not limited to body tissues, but may be used on many surfaces, most notably non-stick surfaces such as TEFLON. Accordingly, industrial applications are possible.

The composition in all forms is made up of hydrolyzed type I collagen having a molecular weight ranging from 1,000 to 10,000. Preferably, the molecular weight will range from 2000 to 4000. Most preferably, it will be in the range of 2500 to 2800. The source of the collagen is preferably bovine, although porcine sources may be used. Most preferably, the bovine source will be calves less than one year of age. Once again, all forms of the compound may be combined with other healing agents especially hyaluronic acid and glycosaminoglycans to speed the healing process further.

The powder form will preferably have a moisture content of approximately 4–7%, and a pH range from 5.5–6.5. The powder will also preferably have an ash content of less than 2.5% by weight and an isotonic point of 5.0–6.5. In use, the powder may be the preferred form for use with irregularly shaped wounds especially since the powder has better hemostatic qualities. Tunnel wounds, flaps, and other non-conformative sites may be managed with the powder because it easily conforms to any shape wound, and may be applied by a poofer bottle or otherwise blown into difficult to reach wound sites. The powder is especially useful in wounds with a large amount of exudate, as the powder can absorb nearly 30 times, its own weight. As the powder absorbs the exudate, a gel is formed which completely fills the wound, forming a mechanical barrier against bacterial infection.

The gel form of the composition is especially useful in wounds with lesser amounts of exudate. The gel is made up of approximately 25–60% hydrolyzed type I collagen and 40–75% water, weight to volume. It is most preferable to use approximately 60% hydrolyzed type I collagen. The gel is formed by the simple addition of water (by volume) to the powdered form (by weight). The gel has the added advantage of adding moisture to the wound site, and has anti-bacterial properties, as indicated in Table 1.

Table 1 displays kill rates for various organisms over time. In testing, cultures were prepared using the following procedure: 1) Prepare overnight broth cultures of each organism using Soybean Casein Digest Broth USP (TSB). 2) Dilute the overnight culture using sterile saline to obtain a 60–65% transmittance. Samples were prepared according to the following procedure: 1) Aseptically weigh 20 grams of the product (gel) in a sterile container. 2) Prepare a control of 20 mL of TSB in a sterile container. Testing is done according to the following procedure: 1) Have prepared adequate volumes of D/E neutralizing broth and molten cooled ($\approx 45°$ C.) Letheen Agar. 2) For each organism: i. vortex the diluted culture and add 0.1 mL to a container containing the gel, mix well; ii. exactly 30 minutes after addition of the culture, vortex and remove 1 mL to a 9 mL D/E broth blank, then continue serial 10-fold dilution in 9 mL sterile saline with Tween-80 blanks through $10^{-8}$; iii. prepare duplicate 1 mL Letheen Agar plate counts from each dilution in ii.; iv. after one hour, vortex and remove 1 mL to a 9 mL D/E blank and again serially dilute 10-fold through $10^{-8}$ in saline with Tween-80 and prepare duplicate 1-mL Letheen Agar plate counts from each dilution. Repeat after 4, 8, 24, and 48 hours; v. repeat i. -iv. adding the culture to the control preparation; vi. incubate all dilution plates at 30–35° C. and check for growth at 24 and 48 hours. 3) Enumerate colonial growth for each organism when the control plates show well-formed colonies. Record data for sample dilution plates showing between 30 and 300 colonies. Calculate the population at each time point for each organism-sample combination.

TABLE 1

Comparative Anti-microbial Efficacy of Gel
Cfu Recovered (% kill rate)

|  | Control count | 30 Min. | 60 Min. | 4 Hrs. | 8 Hrs. | 24 Hrs. | 48 Hrs. |
| --- | --- | --- | --- | --- | --- | --- | --- |
| Staphylococcus aureus | $6.1 \times 10^7$ | $2.6 \times 10^5$ (99.6) | $2.7 \times 10^4$ (99.9+) | $3.5 \times 10^1$ (99.9+) | <10 (99.9+) | <10 (99.9+) | <10 (99.9+) |
| Pseudomonas aeruginosa | $3.8 \times 10^7$ | $7.6 \times 10^4$ (99.8) | $4.2 \times 10^4$ (99.9) | $6.4 \times 10^3$ (99.9+) | <10 (99.9+) | <10 (99.9+) | <10 (99.9+) |
| Escherichia coli | $5.0 \times 10^7$ | $4.0 \times 10^2$ (99.9+) | $4.6 \times 10^3$ (99.9+) | <10 (99.9+) | <10 (99.9+) | <10 (99.9+) | <10 (99.9+) |
| Proteus vulgaris | $2.5 \times 10^9$ | $4.0 \times 10^5$ (99.9+) | $5.5 \times 10^4$ (99.9+) | $1.0 \times 10^3$ (99.9+) | $1.0 \times 10^4$ (99.9+) | <10 (99.9+) | <10 (99.9+) |
| Acinetobacter baumannii | $3.2 \times 10^7$ | <10 (99.9+) | $2.5 \times 10^1$ (99.9+) | <10 (99.9+) | $3.8 \times 10^3$ (99.9+) | <10 (99.9+) | <10 (99.9+) |
| Clostridium sporogenes | $1.8 \times 10^5$ | <10 (99.9+) | <10 (99.9+) | <10 (99.9+) | <10 (99.9+) | <10 (99.9+) | <10 (99.9+) |
| Bacillus subtillus | $1.0 \times 10^4$ | $1.0 \times 10^4$ (99.8) | $1.0 \times 10^4$ (99.8) | $<1.0 \times 10^4$ (>99.8) | $5.0 \times 10^3$ (99.9+) | $7.5 \times 10^1$ (99.9+) | <10 (99.9+) |

A film may be made by mixing, under heat (155–175° F.), the powdered form with deionized water. Cross-linking agents, such as humectant, propylene glycol, sorbitol, glycerine, etc., are added to the mix. A preservative, such as benzyl alcohol or paraben, may also be added. The mixture is subsequently cast on a belt liner knife over a roll coating machine forming a liquid film. The liquid film is then dried in an oven leaving a film which may be applied to a wound site. The film may also be formed by cooling a similar solution. This film form may be used for drug or other chemical delivery, especially in dental applications. Antimicrobial and other medicinal agents may also be added to the film as needed for specific applications.

In practice, the present invention has been shown to be effective, both in humans and animals, as demonstrated by the following case studies. The following case studies are merely exemplary; additional case studies and testimonials are available.

CASE STUDIES

EXPERIMENTAL USE: In an experimental study based on nine (9) animals, wound closure was increased by using the present invention, as illustrated in Table 2. Large gains in wound closure occur near the beginning of treatment, thus reducing the chance of biological infection by reducing the area through which pathogens could enter the body.

TABLE 2

| Days of Treatment | Percent Wound Closure | |
| --- | --- | --- |
| | Control | Experimental |
| 3 | 2% | 19% |
| 5 | 23% | 40% |
| 7 | 51% | 68% |
| 9 | 64% | 79% |

CASE STUDY 1: A white male aged 30 years having a deep chronic ulcer at the right medial malleolus began treatment on Sep. 27, 1996. The wound measured 3.5 cm long by 5.5 cm wide and was 1.5 cm deep. No tunneling existed with minimal drainage visible. Traditional treatment including whirlpool was administered. On Nov. 8, 1996 the wound measured 1.9 cm long by 4.0 cm wide and was 0.6–0.8 cm deep. On Nov. 15, 1996 the wound was grafted by a plastic surgeon. Unfortunately the graft failed, leaving the patient with an open wound. On Jan. 8, 1997 the wound measured 3 cm long by 0.8 cm wide and 0.5 cm deep. Treatment according to the present invention was started by administering the compound once daily. Compression stocking was also used to reduce edema at the ankle and lower leg. On Feb. 10, 1997 it was found that the patient was incorrectly adding hydrogen peroxide to the treatment regime. Electrical stimulation was added once weekly. The wound was irregularly shaped, measuring 1.0 cm long by 1.5 cm wide. On Feb. 25, 1997 the wound measured 1.0 cm long by 1.0 cm wide, still irregularly shaped. Treatment according to the present invention continued. On Mar. 25, 1997 the wound changed shape and appeared less deep. By May 8, 1997 the wound was at skin level, measuring 0.5 cm long by 0.5 cm wide. On May 29, 1997 the wound measured 0.25 cm by 0.25 cm wide with minimal drainage present. On Jul. 1, 1997 Vitamin E was added to the application. By Aug. 5, 1997, 8 months after treatment according to the present invention began, the wound was completely healed.

CASE STUDY 2: A diabetic 77-year-old woman was admitted with a gangrenous right great toe and purple discoloration of the entire foot except the remaining four toes on Jan. 29, 1997. For the next three days, the patient underwent debridement and amputation of the first great toe. On Feb. 3, 1997 with debridement of the forefoot, the wound encompassed nearly 50% of the length of the foot exposing three tendons on the dorsal surface. On Febrero 5, Mesalt treatment was begun and on Febrero 6, the patient was moved to an extended care facility. By Febrero 7, the area of the tendons measured 7.5 cm long by 3.6 cm wide. The Mesalt treatment was stopped on Febrero 11, when treatment according to the present invention began, starting at the dorsum of the foot. Mesalt treatment, for continued debridement, was used on the plantar surface. By Febrero 12, increased granulation was noted on the dorsum wound bed. Tissue coverings over the tendons were improved by Febrero 17. Deposition of tissue over the tendon had increased sufficiently by Feb. 21, 1997 to allow grafting over the tendons, and closure of the plantar area.

CASE STUDY 3: A 69-year-old white male with a long history of venous stasis ulcers began suffering flu-like symptoms on Nov. 11, 1996. He had been using a calcium alginate product on his open ulcers for over a year. On November 4, the patient was treated with antibiotics for a suspected staph infection when presenting a red, swollen left extremity with watery blisters on the dorsum of the foot. On November 9, the patient was admitted to an acute care facility. By November 10, the ulcer over the metatarsal on the dorsum of the foot measured 7.5 cm long by 5 cm wide. The wound was oval shaped with a yellow slough at the base of the wound. Mesalt treatment began on Nov. 14, 1996. The next day, the wound was getting deeper, with three visible tendons. On November 18, whirlpool treatment was administered. A culture taken on November 22 yielded very few Staph A. Treatment according to the present invention was begun. On November 25, patient was admitted to an extended care facility for continued treatment. Patient had a cerebrovascular accident on Dec. 5 and was admitted to acute care. The dorsal wound measured 5 cm long by 2.5 cm wide. The venous stasis ulcer improved. By December 16, the wound measured 2.5 cm long by 1.25 cm wide and was filled to skin level. By Jan. 28, 1997 the dorsal wound and venous stasis ulcers had healed. The wound went from exposed tendons to healed in only two months.

CASE STUDY 4: A 14-year-old 1500 pound thoroughbred gelding presented severe laceration of the right hind leg. Initial examination revealed a 10 by 30 cm wound along the dorsum of the distal hock and metatarsus, extending to the bone completely severing the long distal extensor tendon. The wound was cleaned, debrided, and sutures attempted. Over the course of a year, the horse underwent multiple debridement surgeries, sequestrum removal procedures, and pinch and punch grafting sessions. The wound continued at 15 by 7.5 cm even after one year. Treatment began according to the present invention, applying compound to the wound along with bandage changes every 1 to 3 days. Occasionally, a steroid ointment was used along with treatment. After one month, noticeable epithelialization had occurred and the wound diameter decreased in size to 12.5 by 5 cm. At two months, the wound was noticeably smaller at 9 by 4.5 cm. At three months, further epithelialization had occurred and the wound diameter had reduced to 8 by 4 cm. After six months, and a second traumatic event and laceration of the same region, the wound continues to epithelialize.

It is to be understood that the present invention is not limited to the embodiments described above, but encompasses any and all embodiments within the scope of the following claims.

I claim:

1. A method for applying a wound dressing as a tissue adhesive to aid in healing open wounds, said method consisting essentially of the steps of:
   a. debriding and cleansing an open wound site with a saline solution;
   b. drying surrounding skin, leaving the open wound moist;
   c. applying, generously, a treatment compound of a hydrolyzed type I collagen having an average molecular weight ranging from 1,000 to 10,000 in a form selected from the group consisting of a powder, gel, paste, and film directly to the wound site and surrounding area, wherein said treatment compound comprises a tissue adhesive medical hydrolysate having uncleaved peptide ends;
   d. applying a nonsticking dressing; and
   e. repeating steps b-d at least once every twenty-four hours, wherein removal of previously applied hydrolyzed type I collagen becomes unnecessary.

2. The method as defined in claim 1, wherein said hydrolyzed type I collagen has a molecular weight ranging from 2000 to 4000.

3. The method as defined in claim 2, wherein said hydrolyzed type I collagen has a molecular weight ranging from 2500 to 2800.

4. The method as defined in claim 1, wherein said hydrolyzed type I collagen is derived from a bovine source.

5. The method as defined in claim 4, wherein said bovine source is calves under one year of age.

6. The method as defined in claim 1, wherein said tissue adhesive medical hydrolysate is in powdered form.

7. The method as defined in claim 1, wherein said tissue adhesive medical hydrolysate is in gel form comprising approximately 25–6% hydrolyzed Type I collagen and approximately 40–75% water, weight to volume.

8. The method as defined in claim 7, wherein said gel comprises 60% hydrolyzed Type I collagen and approximately 40% water, weight to volume.

9. The method as defined in claim 1, wherein said tissue adhesive thin layer of hydrolyzed Type I collagen mixed with water and a cross-linking agent.

10. A wound dressing composition including a tissue adhesive medical hydrolysate consisting essentially of a hydrolyzed Type I collagen having an average molecular weight ranging from 1,000 to 10,000 and having a physical form selected from the group consisting of a powder, gel, paste, and film, and having uncleaved peptide ends.

11. The wound dressing as defined in claim 10, wherein said hydrolyzed type I collagen has a molecular weight ranging from 2000 to 4000.

12. The wound dressing as defined in claim 11, wherein said hydrolyzed type I collagen has a molecular weight ranging from 2500 to 2800.

13. The wound dressing as defined in claim 10, wherein said hydrolyzed type I collagen is derived from a bovine source.

14. The wound dressing as defined in claim 13, wherein said bovine source is calves under one year of age.

15. The wound dressing as defined in claim 10, wherein said tissue adhesive medical hydrolysate is in powdered form.

16. The wound dressing as defined in claim 10, wherein said tissue adhesive medical hydrolysate is in gel form comprising approximately 25–60% hydrolyzed Type I collagen, and approximately 40–75% water, weight to volume.

17. The wound dressing as defined in claim 10, wherein said gel comprises 60% hydrolyzed Type I collagen and approximately 40% water, weight to volume.

18. The wound dressing as defined in claim 10, wherein said tissue adhesive medical hydrolysate is in film form made by removing water from a thin layer of hydrolyzed Type I collagen mixed with water and a cross-linking agent selected from the group consisting of humectant, propylene glycol, sorbitol, and glycerine.

19. The wound dressing as defined in claim 18, wherein said film further comprises a medicinal agent.

20. The wound dressing as defined in claim 17, wherein a preservative selected from the group consisting of benzyl alcohol and paraben is added.

* * * * *